United States Patent [19]

Nakaya et al.

[11] 4,211,926
[45] Jul. 8, 1980

[54] TOMOGRAPHIC IMAGING SYSTEM

[75] Inventors: Chitose Nakaya, Hachioji; Hideki Kohno, Tokyo; Hidemi Shiono, Akikawa; Kensuke Sekihara, Tokyo; Shinji Yamamoto, Hachioji; Teruichi Tomura, Kunitachi; Takayuki Hayakawa, Hachioji, all of Japan

[73] Assignee: Hitachi Medical Corporation, Japan

[21] Appl. No.: 901,241

[22] Filed: Apr. 28, 1978

[30] Foreign Application Priority Data

Sep. 2, 1977 [JP] Japan ................. 52-104922

[51] Int. Cl.² ........................................... G03B 41/16
[52] U.S. Cl. ................................. 250/445 T; 250/385
[58] Field of Search ................. 250/445 T, 401, 402, 250/385, 491

[56] References Cited

U.S. PATENT DOCUMENTS

| | | |
|---|---|---|
| 3,778,614 | 12/1973 | Hounsfield . |
| 3,965,357 | 6/1976 | Hounsfield ............... 250/445 T |
| 4,070,707 | 1/1978 | Barber ..................... 250/445 T |
| 4,112,397 | 9/1978 | Randall .................... 250/445 T |
| 4,158,776 | 6/1979 | Barrett ..................... 250/445 T |

Primary Examiner—Craig E. Church
Attorney, Agent, or Firm—Craig & Antonelli

[57] ABSTRACT

In a system in which the tomographic image of an object under investigation is produced on the basis of the amount of absorption of radiation by the object when a source of radiation and a plurality of radiation sensitive detectors with the object interposed therebetween are rotated around the object, the output signal from at least one of the plural detectors is used to correct the radiation absorption amount. Another selected one of the plural detectors may be used for checking whether the object is positioned within a useful detection view.

5 Claims, 3 Drawing Figures

TOMOGRAPHIC IMAGING SYSTEM

This invention relates to an imaging system using divergent radiation such as X-rays or γ-rays and more particularly to a tomographic imaging system using a computer.

Figure 1:
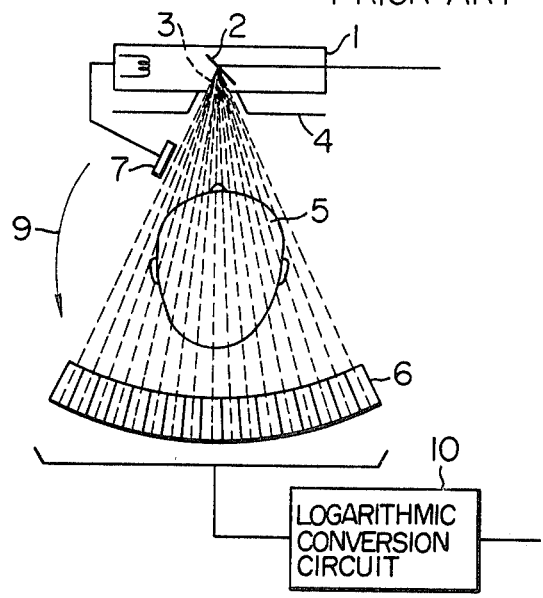
Figure 2:
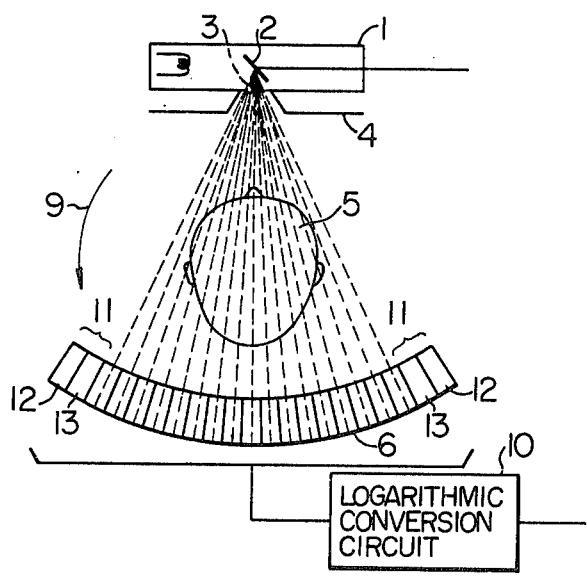
Figure 3:
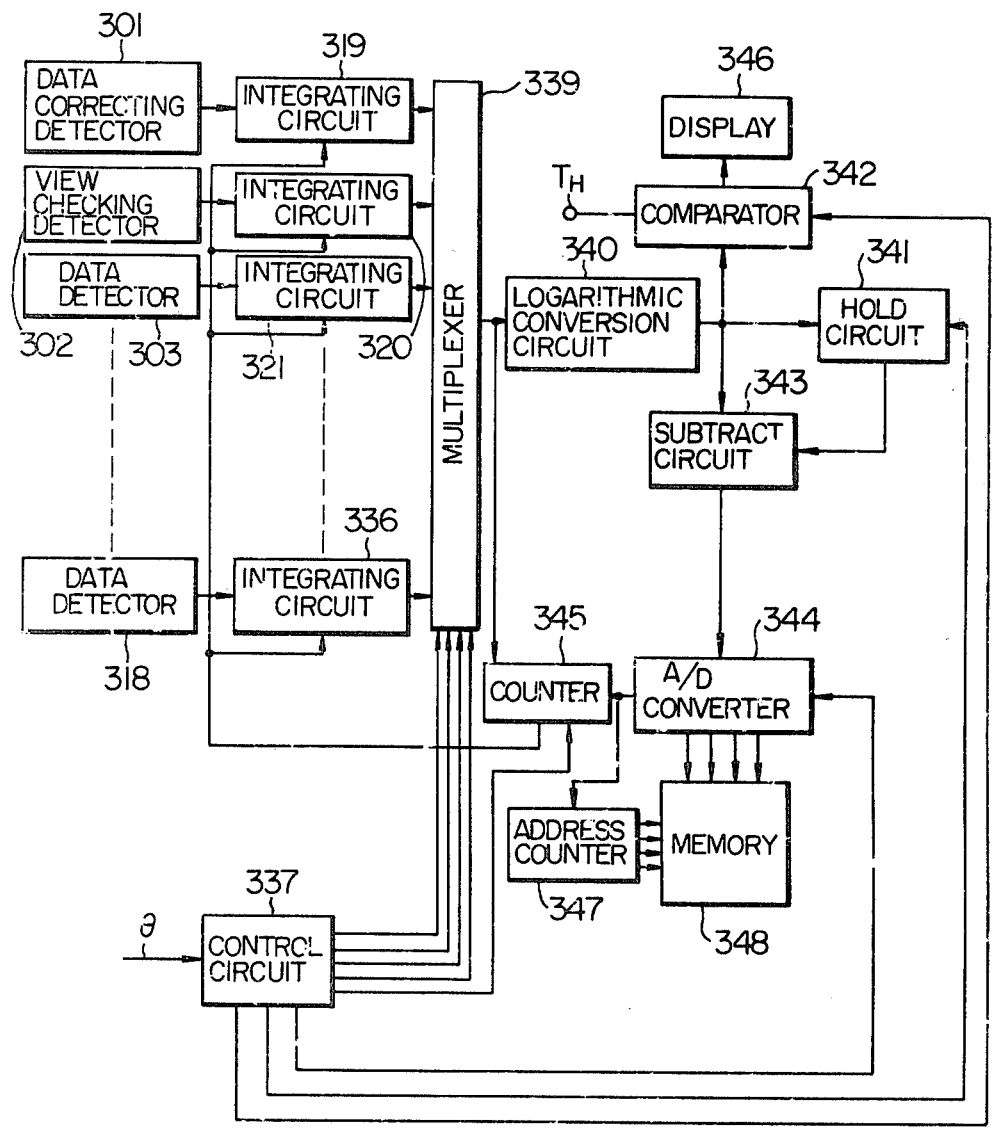

This invention as well as the prior art will be described in conjunction with the accompanying drawings, in which:

FIG. 1 schematically shows a main part of the prior art tomographic imaging system;

FIG. 2 schematically shows a main part of the tomographic imaging system according to an embodiment of this invention; and FIG. 3 is a block diagram explaining the signal processing employed in this invention.

Usually, in a computed X-ray tomographic imaging system, the distribution of X-ray intensities in an object under investigation is converted into an electric signal and this signal is processed to produce a tomographic image.

A typical prior art arrangement for producing an electric signal in such an X-ray tomographic imaging system is illustrated in FIG. 1 which shows a data deriving arrangement for producing a tomographic image of an object 5 under investigation. Referring to FIG. 1, X-rays 3 generated by the cathode 2 of an X-ray source or tube 1 pass through the object 5 via a collimator 4 and then impinge upon a plurality of radiation sensitive detectors 6. A radiation sensitive detector 7 is provided near the collimator 4 to monitor the intensity of X-rays generated from the X-ray tube 1.

In operation, the X-ray tube 1, the detector 7 and the detectors 6 are rotated as shown by arrow 9 while keeping a relative relationship in position with respect to each other. Since the output of the detector 6 exponentially attenuates as is well known, the supplying of the detector output to a logarithmic conversion circuit 10 results in a value corresponding to the X-ray absorption coefficient of the object 5. The detector 7 monitors the variation in intensity of X-rays generated from the X-ray tube 1 to detect this variation as an electric signal so that a correction may be made to data derived from the output signals of the detectors 6.

However, since the output signal of the monitoring detector 7 arranged near the X-ray tube 1 is based on the X-rays almost uninfluenced by the absorption by a layer of air and the detectors 6 and 7 may be different in characteristic from each other, there is a problem that the difference in signal level between these detectors may be considerable, thereby making an appropriate correction impossible and deteriorating the quality of reproduced image.

Another problem in the prior art system is that the object must be positioned within a useful view of the detectors. Otherwise, the quality of reproduced image will be remarkably deteriorated.

An object of this invention is to provide a computed tomographic imaging system which can provide an excellent quality of reproduced image.

According to this invention, there is provided a computed tomographic imaging system in which the tomographic image of an object under investigation is produced by processing output signal data from an array of radiation sensitive detectors when a source of radiation and the detector array with the object interposed therebetween are rotated around the object, wherein said detector array includes at least one radiation sensitive detector for producing an output signal for correction of said output signal data from selected detectors of said detector array.

Said detector array may further include a radiation sensitive detector at at least one of opposite sides of said detector array to check whether said object is positioned within a useful view, i.e., a field of view or scan field of said detector array.

FIG. 2 schematically shows a main part of the tomographic imaging system according to an embodiment of this invention. The same reference numerals are used for equivalent components in FIGS. 1 and 2.

Referring to FIG. 2, detector means 11 including two additional detectors 12 and 13 is shown at each side of an array of data detectors 6 which provide output signal data for producing the tomographic image of the object 5 under investigation. The additional detectors 12 and 13 are provided for improving the quality of reproduced image in accordance with this invention. The detector 12 serves to produce an output signal which is used to correct the output signal data from the data detectors 6. On the other hand, the detector 13 serves to produce an output signal which is used to check whether the object 5 is positioned within a useful view of the data detector array 6 or not. Each of the detectors 6, 12 and 13 may be a well-known spark or gas chamber X-ray detector, as shown in U.S. Pat. No. 4,031,396, which produces an electric signal in response to the ionization of an inert or inactive gas by the impingement of X-rays.

FIG. 3 shows in block diagram a circuit arrangement for producing the output signals from the detectors 6, 12 and 13 shown in FIG. 2. In FIG. 3, a data correcting detector 301 corresponds to the detector 12 of FIG. 2 which provides the output signal for correcting the data measured. A view checking detector 302 corresponds to the detector 13 of FIG. 3 which provides the output signal for checking the field of view of the detector array. Data detectors 303 to 318 correspond to the detectors 6 of FIG. 2 which provide the data for producing the tomographic image of the object. For example, 256 data detectors may be used. For convenience of illustration, only sixteen data detectors are shown.

When an angular signal θ produced by the rotation of the X-ray tube 1 and the detector array in a well-known manner is supplied to a control circuit 337, the control circuit 337 generates an output signal for operating a counter 345 whose output activates or sets integrating circuits 319 to 336. The control circuit 337 also generates address signals to a multiplexer 339, a hold start signal to a hold circuit 341, a comparison start signal to a comparator circuit 342 and an A/D (analog-to-digital) conversion start signal to an A/D converter 344. First, the integrating circuit 319 is activated by the output of the counter 345 so that the output signal from the data correcting detector 301 is integrated for an integration time ΔT. The multiplexer 339 selects the integrating circuit 319 after the time ΔT by the address signal from the control circuit 337 and the integrated value of the output signal of the data correcting detector 301 is subjected to a logarithmic conversion in the logarithmic conversion circuit 340. The logarithmic converted value ln $I_O$ is held in the hold circuit 341 by the hold start signal from the control circuit 337. Next, the integrating circuit 320 is activated so that the output signal from the view checking detector 302 is integrated. The multiplexer 339 selects the integrating circuit 320 after the time ΔT and the integrated value of the output signal of the view checking detector 302 is subjected to a logarithmic conversion in the logarithmic conversion circuit 340. In response to the comparison start signal from the control circuit 337, the logarithmic converted value is compared in the comparator circuit 342 with a predetermined threshold value which is applied to a terminal $T_H$ and represents a useful view of the data detector array 6. If the logarithmic converted value of the output signal of the view checking detector 302 exceeds the threshold value, a suitable indicator or display circuit 346 provides an alarm or visible display to indicate that the measurement is carried out to a view deviated from the useful view or field of view of the detector array.

Assuming that the n-th integrating circuit of the integrating circuits 321 to 336 is activated at time instant t=T. Then, the n-th integrating circuit is selected by the multiplexer 339 at time instant t=T+ΔT. As a result, the integrated output signal of the data detector associated with the selected integrating circuit is applied to the logarithmic conversion circuit 340. The logarithmic converted value ln $I_n$ is subtracted in a subtraction circuit 343 from the value ln $I_O$ previously held in the hold circuit 341. The resulting or corrected value ln $I_O/I_n$ is converted into a digital version by the A/D converter 344. When the A/D conversion operation in the A/D converter 344 has been finished, an output from the A/D converter 344 stops the operation of the counter 345 which in turn resets each of the integrating circuits 319 to 336. The output from the A/D converter 344 also excites the address counter 347 so that the A/D converted output of the A/D converter 344 is stored in a memory 348 at its address designated by the address counter 347.

In the above-described embodiment, whether the object is positioned within a useful view or not has been checked by the comparison of the output of the view checking detector 13 or 302 with the predetermined threshold value in the comparator circuit 342. However, the checking may be carried out in such a manner that the outputs of the detectors 12 or 301 and 13 or 302 are compared and the deviation from the useful view is indicated when the difference between those detector outputs exceeds a predetermined level.

Though in FIG. 2 the detectors 12 and 13 have been provided at the both sides of the data detector array 6, they may be provided at only either one side of the data detector array. Even in such a case, the improvement in the quality of reproduced image can be attained. The number of the detector 12 or 13 is not limited to one. For example, three or four detectors 12 or 13 may be provided. In the case where the detectors 12 and 13 are provided at the both sides of the data detector array 6, the useful view of the object can be enlarged so that X-rays entering into the detectors in the vicinity of the both ends of the data detector array may travel through only a layer of air and the output signal from those detectors may be used for the view check.

The threshold value applied to the comparator circuit 340 from the terminal $T_H$ may be a value of the output signal from any given detector when X-rays travel through the air layer.

Though this invention has been described and shown in conjunction with the case where the tomographic image is produced using the divergent X-rays, it should be understood that this invention is applicable to the tomographic imaging using γ-rays or ultrasonic radiation.

What is claimed is:

1. A tomographic imaging system comprising:
   generating means for generating penetrating radiation toward an object under investigation;
   detecting means including an array of radiation sensitive detectors for detecting the radiation from said generating means transmitted through the object and for providing an output indicative thereof, said detecting means including at at least one side of said detector array of radiation sensitive detectors, a checking detector being responsive to the radiation generated by said generating means which normally does not pass through the object under investigation for checking whether the object is positioned within a field of view of said detector array of radiation sensitive detectors, said checking detector providing an output indicative of the radiation generated which normally does not pass through the object;
   means for comparing the output of said checking detector with a predetermined value for determining whether the object is positioned within the field of view of said detector array;
   means for rotating said generating means and said detecting means while keeping a predetermined relative relationship in position with respect to each other; and
   means for processing the output from said detector array to produce a tomographic image of the object.

2. A tomographic imaging system according to claim 1, wherein each radiation sensitive detector in said detector array is a gas chamber type of detector.

3. A tomographic imaging system according to claim 1, further comprising display means for displaying the output from said checking detector.

4. A tomographic imaging system according to claim 1, wherein a checking detector is provided at each side of said detector array.

5. A tomographic imaging system according to claim 1, wherein said detector array further includes a detector for producing an output signal for correction of the output of selected detectors of said detector array.

* * * * *